United States Patent [19]

Arakawa

[11] Patent Number: 4,573,450
[45] Date of Patent: Mar. 4, 1986

[54] ENDOSCOPE

[75] Inventor: Satoshi Arakawa, Omiya, Japan

[73] Assignee: Fuji Photo Optical Co., Ltd., Saitama, Japan

[21] Appl. No.: 667,770

[22] Filed: Nov. 2, 1984

[30] Foreign Application Priority Data

Nov. 11, 1983 [JP] Japan ................ 58-212947

[51] Int. Cl.[4] .............................................. A61B 1/06
[52] U.S. Cl. ................................... 128/6; 358/98
[58] Field of Search ................ 128/4, 6, 7, 8; 358/98

[56] References Cited

U.S. PATENT DOCUMENTS

| 2,788,390 | 4/1957 | Sheldon | 128/8 X |
| 3,924,608 | 12/1975 | Mitsui | 128/6 X |
| 4,266,534 | 5/1981 | Ogawa | 128/6 |
| 4,491,865 | 1/1985 | Danna et al. | 358/98 |

FOREIGN PATENT DOCUMENTS 3233924  4/1983  Fed. Rep. of Germany .......... 128/6

Primary Examiner—William H. Grieb
Attorney, Agent, or Firm—Koda and Androlia

[57] ABSTRACT

This disclosure depicts an endoscope inserted into a cavity in a human body or a component such as an engine, for observing the interior thereof. In the endoscope according to the present invention, a face plate-shaped image sensor provided on the forward end of an insertion portion can output an optical image obtained through an objective optical system as electric image signals, which can be displayed on a picture plane of a television. This endoscope is disposed on a plane incorporating therein the center axis in the longitudinal direction of the insertion portion, so that the outer diameter of the insertion portion of the endoscope can be reduced in addition to that the size of the image sensor can be secured satisfactorily. Furthermore, in the forward end of the insertion portion of this endoscope according to the present invention, a space sufficient for receiving a forceps channel can be secured at a side opposite to the side, where the objective optical system is disposed, with respect to the image sensor.

6 Claims, 4 Drawing Figures

ENDOSCOPE

BACKGROUND OF THE INVENTION

1. Field of the Invention

This invention relates to an endoscope wherein a face plate-shaped image sensor as a charge coupled device is provided at the forward end portion thereof, and more particularly to an endoscope wherein an article to be observed is displayed on a picture plane of a television for the observation on the basis of image signals obtained through the charge coupled device.

2. Description of the Prior Art

In most cases, the conventional endoscopes have been each constructed such that an objective lens and an eye piece are disposed at opposite end portions of optical fibers for transmitting an image, an image of an article to be observed is made to focus at one end face of the optical fibers and a transmitted image being transmitted through the optical fibers and appearing on the other end face is observed through the eye piece.

While, there has recently been studied a television endoscope utilizing a face plate-shaped image sensor in which a charge transfer device as typified by a charge coupled device is combined with fine light-receiving elements being matrix-arranged. The television endoscope of the type described is advantageous in every respects of that the durability is high, various processings can be applied to electric signals as being image outputs and the use of the endoscope of this type results in a decrease in cost as compared with the conventional endoscope utilizing image guide fibers. In consequence, it has been studied to put the endoscope of this type in the practical use.

Now, the face plate-shaped image sensor used as the charge coupled device arranged at the forward end of the television endoscope has been rendered compact in size due to the improvements in the manufacturing technique and the degree of integration in recent years, however, it cannot be said that the image sensor has been satisfactorily compact in size to be applied to the endoscope. This is because, as well known, the outer diameter of the endoscope should be so small as to be inserted into a cavity in a human body. It is desirable that the outer diameter of a gastric endoscope is about 10 mm or less, for example. Further, even if the image sensor is satisfactorily rendered compact in size, there still is a requirement for the improvements in the resolving power, i.e. an increase in the number of picture elements on the other hand. This requirement may cause the image sensor to be more or less increased in size.

With the above-described circumstances being for a background, in constructing a television endoscope, it becomes an important point how to construct the forward end portion of the endoscope, i.e. how to efficiently arrange the image sensor and the objective optical system for making an optical image be made to focus at the image sensor within a limited space. As a typical construction of the forward end portion of a direct vision endoscope, which has been under study, there is such one in which a face plate-shaped image sensor is disposed on a plane perpendicularly intersecting the longitudinal direction of the end scope and an optical image from a direct vision objective optical system is made to focus at the image sensor as it is. As a typical construction of the forward end portion of a side vision endoscope, which has also been under study, there is such one in which the image sensor is disposed along the longitudinal direction and close to one side wall surface of the endoscope and an optical image from a side vision objective optical system is made to focus at the image sensor. However, when the image sensors are practically assembled into the forward end constructions of the two types described above, there may occur problems. Namely, with the former, when the cross section of the forward end portion is considered, most of the cross sectional area is occupied by the face plate of the image sensor, whereby it becomes very difficult to provide members other than the face plate such for example as a light guide channel, a forceps channel and an air-supply and water-supply channel. Whereas, with the latter, the face plate of the image sensor is disposed close to one side of the endoscope and the optical image from the side vision objective optical system provided at the other side is made to focus at the face plate of the image sensor, whereby, when consideration is given to the cross section of the forward end portion, most of the cross sectional area is occupied by the side vision objective optical system, and moreover, the face plate of the image sensor is disposed close to one side wall of the endoscope, the cross section of which is preferably of a substantially circular shape, so that the cross section of the endoscope may be expected to be deformed to a considerable extent.

SUMMARY OF THE INVENTION

The present invention has been developed to obviate the above-described disadvantages of the prior art and has as its object the provision of an endoscope wherein the construction of the forward end portion of the television endoscope, particularly the arrangement of the face plate-shaped image sensor, and the construction and arrangement of the objective optical system are efficiently carried out, so that the insertion portion of the television endoscope can be reduced in the outer diameter thereof.

To this end, the present invention contemplates that the face plate-shaped image sensor is disposed along the longitudinal direction (direction of insertion) of the endoscope and on a plane incorporating therein the center axis thereof, and further, an optical image is made to focus at the image sensor through a light path changing member such as a prism. It should be readily understood by those skilled in the art that from the description which will be made hereunder that the position of the face plate of the image sensor as described above need not strictly be disposed on the plane incorporating therein the center axis, and any other light path changing member such as a mirror can be utilized in place of the prism.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and therein.

DETAILED DESCRIPTION OF THE INVENTION

Figure 1:
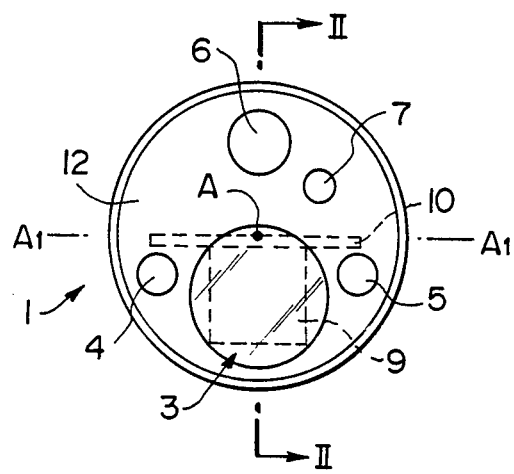
FIG. 1 is a front view showing the forward end portion of the endoscope as one embodiment of the present invention.
Figure 2:
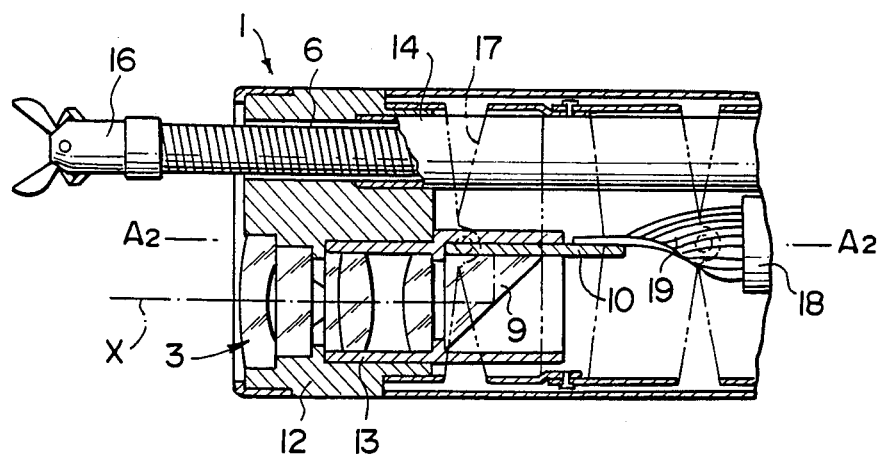
FIG. 2 is a longitudinal sectional view taken along the line II—II in FIG. 1.

Description will hereunder be given of the preferred embodiments of an endoscope according to the present invention with reference to the accompanying drawings. FIGS. 1 and 2 are a front view and a longitudinal sectional view respectively showing the forward end portions of one embodiment, in which the present invention is applied to a direct vision type endoscope. As shown in FIG. 1, inserted through the forward end portion 1 of the endoscope in the longitudinal axial direction (from the right to the left in FIG. 2) of the endoscope are light guide channels 4 and 5, a forceps channel 6 and an air-supply and water-supply channel 7 in addition to an objective optical system 3. As apparent from FIG. 2 showing a section taken along the line II—II in FIG. 1, the objective optical system 3 is constituted by a plurality of lenses. However, according to the present invention, a rectangular prism 9 is provided behind the objective optical system 3, whereby the light path of the axis X of the objective optical system 3 is changed through 90°. A rectangular face plate-shaped image sensor 10 is joined to a light exiting surface of the objective optical system 3.

With the above arrangement, the image sensor 10 is positioned close to and along a plane incorporating therein the center line (the line $A_1$—$A_1$ in FIG. 1 and the line $A_2$—$A_2$ in FIG. 2) of the endoscope, so that the outer diameter of the endoscope can be utilized most effectively. Additionally, the joint of the image sensor 10 to the prism 9 makes it possible to obtain the dust excluding effect, however, the joint should not necessarily be needed, and a lens or a mask may be interposed between the image sensor 10 and the prism 9 for example. Further, a mirror may be used in place of the prism 9, and the change of the light path need not strictly limited to 90° and a small allowance should naturally be permitted. Respective optical parts constituting the objective optical system 3 may be directly fixed to a forward end metal fitting 12 or fixed thereto through a mirror frame 13. Openings for other channels are formed in the fitting 12. For example, connected to the forceps channel 6 as shown in FIG. 2 is a forceps tube 14, through which a forceps is inserted for use. Furthermore, hypothetical lines 17 indicate annular ring members being curved in the vertical and lateral directions by a well known control wire, not shown. Designated at 18 is a circuit unit including a scan driver circuit for driving the image sensor 10 or a circuit for amplifying and A/D (analogue/digital) converting the signals from the image sensor 10, and electrically connected to the image sensor 10 through a web-shaped flexible printed board 19. Needless to say, the circuit unit may be provided on the base board of the image sensor 10 as a hybrid circuit. However, when the curved portion of the endoscope is needed in a spacewise manner, it is desirable that the circuit unit be divided per annular ring member so as not to hinder the curving operation of the annular ring member 17, or it is preferable that the printed board 19 be connected in a manner to be twisted through 90° so as to be able to follow the curving operation of the annular ring members in the vertical and lateral directions.

With the above arrangement, the image sensor 10 as large in the size of one side thereof as the outer diameter of the forward end portion of the endoscope can be thoroughly received. Furthermore, the other side opposite to the side, where the objective optical system is provided, with respect to the image sensor 10, can be utilized as a space not relating to the image pick-up system. In this space, the forceps channel 6, the air-supply and water-supply channel 7 and the like, which require comparatively large installation spaces, can be freely disposed.

Figure 3:
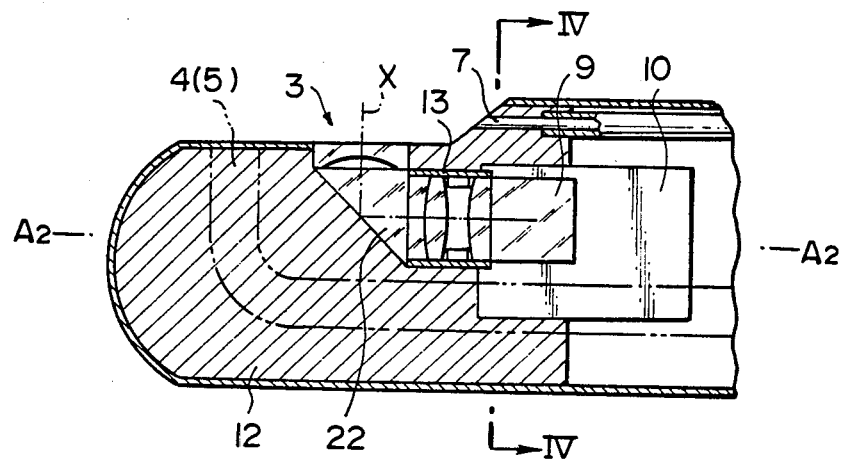
FIG. 3 is a longitudinal sectional view showing the forward end portion of the endoscope as another embodiment of the present invention.
Figure 4:
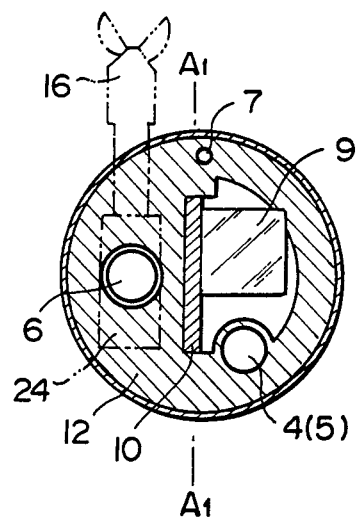
FIG. 4 is a cross-sectional view taken along the line IV—IV in FIG. 3.

FIGS. 3 and 4 are a longitudinal sectional view and a cross-sectional view (the cross-section taken along the line IV—IV in FIG. 3) respectively showing one embodiment, in which the present invention is applied to a side vision type endoscope. In this embodiment, same reference numerals in FIGS. 1 and 2 are used to designate same or similar parts corresponding to ones as shown in FIGS. 1 and 2. In this embodiment also, the image sensor 10 is disposed along the plane incorporating therein the center line (the line $A_2$—$A_2$ in FIG. 3 and the line $A_1$—$A_1$ in FIG. 4) of the endoscope. In the objective optical system 3 as shown here, there is provided a prism 22 for the side vision in addition to the prism 9 having the light emitting surface opposed to the image sensor 10. In the illustrated embodiment, the change of light path by the prism 22 is along the paper surface, while the change of light path by the prism 9 is perpendicular to the paper surface. This arrangement is particularly useful in the case of providing the forceps channel 6. This is because, generally, in the side vision type endoscope, there is a requirement for shortening a rigid forward end portion by the provision of a portion, from which the forceps is led out, at one side of an observation window of the objective optical system 3 and another requirement for providing a forceps control device in the side vision type endoscope, which requires a comparatively large installation space at the portion, from which the forceps is led out. More specifically, as apparent from FIG. 4, the disposition of the image sensor 10 along the erecting direction of the forceps 16 makes it possible for the space at the left side thereof to be utilized as the space for the forceps control device 24 with enough room. However, if the image sensor 10 is set aside to the left side of the center line $A_1$—$A_1$ in FIG. 4, then a restriction may be imposed when the forceps control device 24 is provided. In consequence, when the forceps control device 24 is shifted in front or at the back of the observation window, the forceps control device need not necessarily be disposed in the direction of the light path change of the prism 9 in the illustrated embodiment.

As has been detailedly described hereinabove, according to the present invention, such an arrangement is adopted that the face plate-shaped image sensor is used together with the prism for the change of light path so as to dispose the image sensor in the longitudinal direction of the endoscope, and moreover, the image sensor is located close to the plane incorporating therein the center axis in the longitudinal direction of the endoscope, so that the image sensor having the size as large as the outer diameter of the endoscope can be thoroughly received and the space can be taken with enough room.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope capable of outputting an optical image obtained through an objective optical system as electric image signals by means of a face plate-like image sensor provided on the forward end of an insertion portion, comprising:

said objective optical system provided on the forward end of the insertion portion;

a light path changing member for changing the light path of an image pick-up light from said objective optical system into a direction perpendicular to the longitudinal direction of said insertion portion; and a face plate-shaped image sensor opposed to a light emitting surface of said light path changing member and disposed on a plane incorporating therein the center axis in the longitudinal direction of said insertion portion.

2. An endoscope as set forth in claim 1, wherein said light path changing member comprises a prism or a mirror.

3. An endoscope as set forth in claim 2, wherein a forceps channel is disposed at the other side of the prism of said face plate-shaped image sensor opposed to the light emitting surface of said prism.

4. An endoscope as set forth in claim 1, wherein an observation window is formed in front of said insertion portion so as to form a direct vision type endoscope.

5. An endoscope as set forth in claim 1, wherein an observation window is formed at one side of said insertion portion ahd a prism for the side vision is provided, to thereby form a side vision type endoscope.

6. An endoscope as set forth in claim 5, wherein a forceps channel and a forceps control device are disposed in a space at a side opposite to the side where the objective optical system is disposed with respect to said face plate-shaped image sensor.

* * * * *